(12) United States Patent  (10) Patent No.: US 9,414,822 B2
Ziobro et al.  (45) Date of Patent: Aug. 16, 2016

(54) TISSUE EVERSION APPARATUS AND TISSUE CLOSURE DEVICE AND METHODS FOR USE THEREOF

(75) Inventors: John M. Ziobro, Sunnyvale, CA (US); Wouter E. Roorda, Palo Alto, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 448 days.

(21) Appl. No.: 13/111,403

(22) Filed: May 19, 2011

(65) Prior Publication Data

US 2012/0296374 A1 Nov. 22, 2012

(51) Int. Cl.
*A61B 17/00* (2006.01)
*A61B 17/11* (2006.01)

(52) U.S. Cl.
CPC ..... *A61B 17/0057* (2013.01); *A61B 2017/0065* (2013.01); *A61B 2017/00659* (2013.01); *A61B 2017/00668* (2013.01); *A61B 2017/1121* (2013.01)

(58) Field of Classification Search
CPC ....................................................... A61B 17/00
USPC ....................................................... 606/213
See application file for complete search history.

(56) References Cited

U.S. PATENT DOCUMENTS

| | | | |
|---|---|---|---|
| 1,242,139 A | 10/1917 | Callahan | |
| 1,480,935 A | 1/1924 | Gleason | |
| 2,108,206 A | 2/1938 | Meeker | |
| 2,371,978 A | 3/1945 | Perham | |
| 2,610,631 A | 9/1952 | Calicchio | |
| 3,348,595 A | 10/1967 | Stevens, Jr. | |
| 3,357,070 A | 12/1967 | Sloan | |
| 3,682,180 A | 8/1972 | McFarlane | |
| 3,760,810 A | 9/1973 | Van Hoorn | |
| 3,814,104 A | 6/1974 | Irnich et al. | |
| 3,856,018 A | 12/1974 | Perisse et al. | |
| 3,874,388 A | 4/1975 | King et al. | |
| 3,908,662 A | 9/1975 | Razgulov et al. | |
| 3,926,194 A | 12/1975 | Greenberg et al. | |
| 3,939,820 A | 2/1976 | Grayzel | |
| 3,985,138 A | 10/1976 | Jarvik | |

(Continued)

FOREIGN PATENT DOCUMENTS

| FR | 2768324 | 3/1999 |
|---|---|---|
| JP | 2000014634 A | 1/2000 |

(Continued)

OTHER PUBLICATIONS

U.S. Appl. No. 60/711,279, filed Aug. 24, 2005, Sibbitt, Jr et al.

(Continued)

*Primary Examiner* — Vy Bui
(74) *Attorney, Agent, or Firm* — Workman Nydegger; Randy Shen

(57) ABSTRACT

Methods and apparatuses for closure of vascular punctures or other openings in bodily tissues. The apparatuses and methods described herein are configured for everting a portion of tissue around a puncture site for wound closure on the external surface of the wound. For example, the tissue eversion apparatus may be configured for drawing up a portion of a vessel surrounding a venous or arterial puncture and orienting the inner surface of the vessel at least partially outward so that a closure element may be placed around the inverted region on the exterior surface of the vessel. In some embodiments, the devices are bioabsorbable.

23 Claims, 8 Drawing Sheets

(56) References Cited

U.S. PATENT DOCUMENTS

| | | |
|---|---|---|
| 4,011,872 A | 3/1977 | Komiya |
| 4,018,228 A | 4/1977 | Goosen |
| 4,018,229 A | 4/1977 | Komiya |
| 4,189,808 A | 2/1980 | Brown |
| 4,267,995 A | 5/1981 | McMillan |
| 4,501,276 A | 2/1985 | Lombardi |
| 4,697,312 A | 10/1987 | Freyer |
| 4,830,002 A | 5/1989 | Semm |
| 5,041,129 A | 8/1991 | Hayhurst et al. |
| 5,059,201 A | 10/1991 | Asnis |
| 5,100,422 A | 3/1992 | Berguer et al. |
| 5,133,360 A | 7/1992 | Spears |
| 5,176,691 A | 1/1993 | Pierce |
| 5,192,287 A | 3/1993 | Fournier et al. |
| 5,217,471 A | 6/1993 | Burkhart |
| 5,237,996 A | 8/1993 | Waldman et al. |
| 5,254,105 A | 10/1993 | Haaga |
| 5,290,284 A | 3/1994 | Adair |
| 5,300,078 A | 4/1994 | Buelna |
| 5,330,445 A | 7/1994 | Haaga |
| 5,336,231 A | 8/1994 | Adair |
| 5,354,279 A | 10/1994 | Hofling |
| 5,383,905 A | 1/1995 | Golds et al. |
| 5,403,330 A | 4/1995 | Tuason |
| 5,403,331 A | 4/1995 | Chesterfield et al. |
| 5,404,621 A | 4/1995 | Heinke |
| 5,425,740 A | 6/1995 | Hutchinson, Jr. |
| 5,462,561 A | 10/1995 | Voda |
| 5,466,241 A | 11/1995 | Leroy et al. |
| 5,478,353 A | 12/1995 | Yoon |
| 5,478,354 A | 12/1995 | Tovey et al. |
| 5,486,186 A | 1/1996 | Yoon |
| 5,489,288 A | 2/1996 | Buelna |
| 5,492,119 A | 2/1996 | Abrams |
| 5,507,744 A | 4/1996 | Tay et al. |
| 5,536,267 A | 7/1996 | Edwards et al. |
| 5,562,684 A | 10/1996 | Kammerer |
| 5,571,120 A | 11/1996 | Yoon |
| 5,573,540 A | 11/1996 | Yoon |
| 5,609,597 A | 3/1997 | Lehrer |
| 5,613,974 A | 3/1997 | Andreas et al. |
| 5,613,975 A | 3/1997 | Christy |
| 5,643,318 A | 7/1997 | Tsukernik et al. |
| 5,647,372 A | 7/1997 | Tovey et al. |
| 5,649,959 A | 7/1997 | Hannam et al. |
| 5,669,935 A | 9/1997 | Rosenman et al. |
| 5,672,174 A | 9/1997 | Gough et al. |
| 5,674,231 A | 10/1997 | Green et al. |
| 5,693,061 A | 12/1997 | Pierce et al. |
| 5,713,899 A | 2/1998 | Marnay et al. |
| 5,728,143 A | 3/1998 | Gough et al. |
| 5,735,736 A | 4/1998 | Volk |
| 5,749,898 A | 5/1998 | Schulze et al. |
| 5,759,189 A | 6/1998 | Ferragamo et al. |
| 5,766,217 A | 6/1998 | Christy |
| 5,782,861 A | 7/1998 | Cragg et al. |
| 5,792,151 A | 8/1998 | Heck et al. |
| 5,797,928 A | 8/1998 | Kogasaka |
| 5,797,929 A | 8/1998 | Andreas et al. |
| 5,810,845 A | 9/1998 | Yoon |
| 5,814,052 A | 9/1998 | Nakao et al. |
| 5,817,113 A | 10/1998 | Gifford, III et al. |
| 5,845,657 A | 12/1998 | Carberry et al. |
| 5,855,576 A | 1/1999 | LeVeen et al. |
| 5,861,005 A | 1/1999 | Kontos |
| 5,865,791 A | 2/1999 | Whayne et al. |
| 5,873,876 A | 2/1999 | Christy |
| 5,897,487 A | 4/1999 | Ouchi |
| 5,906,620 A | 5/1999 | Nakao et al. |
| 5,906,631 A | 5/1999 | Imran |
| 5,919,207 A | 7/1999 | Taheri |
| 5,944,728 A | 8/1999 | Bates |
| 5,957,936 A | 9/1999 | Yoon et al. |
| 5,957,938 A | 9/1999 | Zhu et al. |
| 5,964,782 A * | 10/1999 | Lafontaine et al. ............ 606/213 |
| 5,972,009 A | 10/1999 | Fortier et al. |
| 5,976,161 A | 11/1999 | Kirsch et al. |
| 5,984,950 A | 11/1999 | Cragg et al. |
| 5,993,466 A | 11/1999 | Yoon |
| 5,993,476 A | 11/1999 | Groiso |
| 6,009,877 A | 1/2000 | Edwards |
| 6,022,372 A | 2/2000 | Kontos |
| 6,024,747 A | 2/2000 | Kontos |
| 6,056,744 A | 5/2000 | Edwards |
| 6,059,719 A | 5/2000 | Yamamoto et al. |
| 6,068,603 A | 5/2000 | Suzuki |
| 6,083,242 A | 7/2000 | Cook |
| 6,095,155 A | 8/2000 | Criscuolo |
| 6,120,513 A | 9/2000 | Bailey et al. |
| 6,120,524 A | 9/2000 | Taheri |
| 6,126,675 A | 10/2000 | Shchervinsky et al. |
| 6,136,010 A | 10/2000 | Modesitt et al. |
| 6,143,004 A | 11/2000 | Davis et al. |
| 6,152,936 A | 11/2000 | Christy et al. |
| 6,161,263 A | 12/2000 | Anderson |
| 6,165,204 A | 12/2000 | Levinson et al. |
| 6,178,355 B1 | 1/2001 | Williams et al. |
| 6,197,042 B1 | 3/2001 | Ginn et al. |
| 6,221,084 B1 | 4/2001 | Fleenor |
| 6,248,124 B1 | 6/2001 | Pedros et al. |
| 6,296,657 B1 | 10/2001 | Brucker |
| 6,306,081 B1 | 10/2001 | Ishikawa et al. |
| 6,315,782 B1 | 11/2001 | Chu et al. |
| 6,322,580 B1 | 11/2001 | Kanner |
| 6,358,258 B1 | 3/2002 | Arcia et al. |
| 6,395,015 B1 | 5/2002 | Borst et al. |
| 6,397,110 B1 | 5/2002 | Kuzma |
| 6,428,472 B1 | 8/2002 | Haas |
| 6,443,963 B1 | 9/2002 | Baldwin et al. |
| 6,461,366 B1 | 10/2002 | Seguin |
| 6,482,224 B1 | 11/2002 | Michler et al. |
| 6,506,209 B2 | 1/2003 | Ouchi |
| 6,517,498 B1 | 2/2003 | Burbank et al. |
| 6,533,812 B2 | 3/2003 | Swanson et al. |
| 6,547,806 B1 | 4/2003 | Ding |
| 6,569,159 B1 | 5/2003 | Edwards et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,599,311 B1 | 7/2003 | Biggs et al. |
| 6,610,072 B1 | 8/2003 | Christy et al. |
| 6,613,060 B2 | 9/2003 | Adams et al. |
| 6,623,509 B2 | 9/2003 | Ginn |
| 6,623,510 B2 | 9/2003 | Carley et al. |
| 6,626,918 B1 | 9/2003 | Ginn et al. |
| 6,663,655 B2 | 12/2003 | Ginn et al. |
| 6,676,685 B2 | 1/2004 | Pedros et al. |
| 6,679,904 B2 | 1/2004 | Gleeson et al. |
| 6,689,051 B2 | 2/2004 | Nakada et al. |
| 6,695,867 B2 | 2/2004 | Ginn et al. |
| 6,736,822 B2 | 5/2004 | McClellan et al. |
| 6,743,195 B2 | 6/2004 | Zucker |
| 6,743,259 B2 | 6/2004 | Ginn |
| 6,745,079 B2 | 6/2004 | King |
| 6,746,457 B2 | 6/2004 | Dana et al. |
| 6,749,621 B2 | 6/2004 | Pantages et al. |
| 6,749,622 B2 | 6/2004 | McGuckin, Jr. et al. |
| 6,767,356 B2 | 7/2004 | Kanner et al. |
| 6,776,785 B1 | 8/2004 | Yencho et al. |
| 6,837,906 B2 | 1/2005 | Ginn |
| 6,846,319 B2 | 1/2005 | Ginn et al. |
| 6,849,078 B2 | 2/2005 | Durgin et al. |
| 6,890,343 B2 | 5/2005 | Ginn et al. |
| 6,896,692 B2 | 5/2005 | Ginn et al. |
| 6,904,647 B2 | 6/2005 | Byers, Jr. |
| 6,942,674 B2 | 9/2005 | Belef et al. |
| 6,969,397 B2 | 11/2005 | Ginn |
| 6,984,238 B2 | 1/2006 | Gifford, III et al. |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,083,635 B2 | 8/2006 | Ginn |
| 7,112,225 B2 | 9/2006 | Ginn |

(56) References Cited

U.S. PATENT DOCUMENTS

| | | | |
|---|---|---|---|
| 7,122,002 B2 | 10/2006 | Okada | |
| 7,147,646 B2 | 12/2006 | Dana et al. | |
| 7,270,672 B1 | 9/2007 | Singer | |
| 7,316,704 B2 | 1/2008 | Bagaoisan et al. | |
| 7,326,230 B2 | 2/2008 | Ravikumar | |
| 7,331,979 B2 | 2/2008 | Khosravi et al. | |
| 7,335,220 B2 | 2/2008 | Khosravi et al. | |
| 7,338,514 B2 | 3/2008 | Wahr et al. | |
| 7,361,183 B2 | 4/2008 | Ginn | |
| 7,361,185 B2 | 4/2008 | O'Malley et al. | |
| 7,393,363 B2 | 7/2008 | Ginn | |
| 7,396,359 B1 | 7/2008 | Derowe et al. | |
| 7,431,727 B2 | 10/2008 | Cole et al. | |
| 7,507,200 B2 | 3/2009 | Okada | |
| 7,645,285 B2 | 1/2010 | Cosgrove et al. | |
| 7,648,493 B2 | 1/2010 | Forsberg et al. | |
| 7,727,249 B2 | 6/2010 | Rahmani | |
| 7,731,655 B2 | 6/2010 | Smith et al. | |
| 7,749,249 B2 | 7/2010 | Gelbart et al. | |
| 7,799,042 B2 | 9/2010 | Williamson, IV et al. | |
| 7,901,428 B2 | 3/2011 | Ginn et al. | |
| 8,007,504 B2 | 8/2011 | Zenati et al. | |
| 8,048,108 B2 | 11/2011 | Sibbitt, Jr. et al. | |
| 8,226,666 B2 | 7/2012 | Zarbatany et al. | |
| 8,469,969 B2 | 6/2013 | Kear et al. | |
| 8,480,687 B2 * | 7/2013 | Ducharme et al. | 606/140 |
| 2001/0046518 A1 | 11/2001 | Sawhney | |
| 2001/0053909 A1 | 12/2001 | Nakada | |
| 2002/0099389 A1 | 7/2002 | Michler et al. | |
| 2002/0106409 A1 | 8/2002 | Sawhney et al. | |
| 2002/0188275 A1 | 12/2002 | McGuckin, Jr. | |
| 2003/0187457 A1 | 10/2003 | Weber | |
| 2003/0233095 A1 | 12/2003 | Urbanski et al. | |
| 2004/0009205 A1 | 1/2004 | Sawhney | |
| 2004/0093027 A1 | 5/2004 | Fabisiak et al. | |
| 2004/0098044 A1 | 5/2004 | Van de Moer et al. | |
| 2004/0116943 A1 | 6/2004 | Brandt et al. | |
| 2004/0122349 A1 | 6/2004 | Lafontaine et al. | |
| 2004/0127940 A1 | 7/2004 | Ginn et al. | |
| 2004/0143290 A1 | 7/2004 | Brightbill | |
| 2004/0158127 A1 | 8/2004 | Okada | |
| 2004/0158287 A1 | 8/2004 | Cragg et al. | |
| 2004/0167511 A1 | 8/2004 | Buehlmann et al. | |
| 2004/0191277 A1 | 9/2004 | Sawhney et al. | |
| 2004/0215232 A1 | 10/2004 | Belhe et al. | |
| 2004/0225194 A1 | 11/2004 | Smith et al. | |
| 2004/0236354 A1 | 11/2004 | Seguin | |
| 2004/0267193 A1 | 12/2004 | Bagaoisan et al. | |
| 2004/0267308 A1 | 12/2004 | Bagaoisan et al. | |
| 2005/0010248 A1 | 1/2005 | Lafontaine | |
| 2005/0033359 A1 | 2/2005 | Dycus | |
| 2005/0075665 A1 | 4/2005 | Brenzel et al. | |
| 2005/0085851 A1 | 4/2005 | Fiehler et al. | |
| 2005/0085854 A1 | 4/2005 | Ginn | |
| 2005/0085855 A1 | 4/2005 | Forsberg | |
| 2005/0090859 A1 | 4/2005 | Ravikumar | |
| 2005/0121042 A1 | 6/2005 | Belhe et al. | |
| 2005/0149065 A1 | 7/2005 | Modesitt | |
| 2005/0149117 A1 | 7/2005 | Khosravi et al. | |
| 2005/0177189 A1 | 8/2005 | Ginn et al. | |
| 2005/0222614 A1 | 10/2005 | Ginn et al. | |
| 2005/0234396 A1 | 10/2005 | Forsberg et al. | |
| 2005/0245876 A1 | 11/2005 | Khosravi et al. | |
| 2005/0256532 A1 | 11/2005 | Nayak et al. | |
| 2005/0261708 A1 | 11/2005 | Pasricha et al. | |
| 2005/0267528 A1 | 12/2005 | Ginn et al. | |
| 2005/0273137 A1 | 12/2005 | Ginn | |
| 2006/0034930 A1 | 2/2006 | Khosravi et al. | |
| 2006/0047313 A1 | 3/2006 | Khanna et al. | |
| 2006/0058844 A1 | 3/2006 | White et al. | |
| 2006/0089635 A1 | 4/2006 | Young et al. | |
| 2006/0095029 A1 | 5/2006 | Young et al. | |
| 2006/0100664 A1 | 5/2006 | Pai et al. | |
| 2006/0106420 A1 | 5/2006 | Dolan et al. | |
| 2006/0253037 A1 | 11/2006 | Ginn et al. | |
| 2006/0253072 A1 | 11/2006 | Pai et al. | |
| 2006/0259049 A1 | 11/2006 | Harada et al. | |
| 2007/0049967 A1 | 3/2007 | Sibbitt, Jr. et al. | |
| 2007/0049968 A1 * | 3/2007 | Sibbitt et al. | 606/213 |
| 2007/0060895 A1 | 3/2007 | Sibbitt, Jr. et al. | |
| 2007/0060950 A1 | 3/2007 | Khosravi et al. | |
| 2007/0060951 A1 | 3/2007 | Shannon | |
| 2007/0083231 A1 | 4/2007 | Lee | |
| 2007/0123817 A1 | 5/2007 | Khosravi et al. | |
| 2007/0123936 A1 | 5/2007 | Goldin et al. | |
| 2007/0198058 A1 | 8/2007 | Gelbart et al. | |
| 2007/0203506 A1 | 8/2007 | Sibbitt, Jr. et al. | |
| 2007/0213747 A1 | 9/2007 | Monassevitch et al. | |
| 2008/0004636 A1 | 1/2008 | Walberg et al. | |
| 2008/0009794 A1 | 1/2008 | Bagaoisan et al. | |
| 2008/0045979 A1 | 2/2008 | Ma | |
| 2008/0065151 A1 | 3/2008 | Ginn | |
| 2008/0065152 A1 | 3/2008 | Carley | |
| 2008/0287967 A1 | 11/2008 | Andreas et al. | |
| 2008/0287988 A1 | 11/2008 | Smith et al. | |
| 2009/0088794 A1 | 4/2009 | LaFontaine | |
| 2009/0105728 A1 * | 4/2009 | Noda et al. | 606/139 |
| 2009/0157101 A1 | 6/2009 | Reyes et al. | |
| 2009/0306681 A1 | 12/2009 | Del Nido et al. | |
| 2010/0130965 A1 | 5/2010 | Sibbitt, Jr. et al. | |
| 2010/0234884 A1 | 9/2010 | Lafontaine et al. | |
| 2011/0066163 A1 | 3/2011 | Cho et al. | |
| 2012/0245603 A1 * | 9/2012 | Voss | 606/151 |

FOREIGN PATENT DOCUMENTS

| | | |
|---|---|---|
| JP | 2005218868 A | 8/2005 |
| WO | WO 96/40356 | 12/1996 |
| WO | WO 00/56226 | 9/2000 |
| WO | WO 02/062234 | 8/2002 |
| WO | WO 03/094748 | 11/2003 |
| WO | WO 2005/000126 | 1/2005 |
| WO | WO 2005/041782 | 5/2005 |
| WO | WO 2005/063129 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

U.S. Appl. No. 60/726,985, filed Oct. 14, 2005, Sibbitt, Jr. et al.
U.S. Appl. No. 61/097,072, filed Sep. 15, 2008, Sibbitt, Jr. et al.
U.S. Appl. No. 11/316,775, Apr. 16, 2008, Office Action.
U.S. Appl. No. 11/316,775, Aug. 6, 2008, Office Action.
U.S. Appl. No. 11/508,656, Dec. 9, 2009, Restriction Requirement.
U.S. Appl. No. 11/508,656, Mar. 25, 2010, Office Action.
U.S. Appl. No. 11/508,656, Aug. 30, 2010, Office Action.
U.S. Appl. No. 11/508,656, Feb. 10, 2014, Notice of Allowance.
U.S. Appl. No. 11/508,662, Dec. 28, 2009, Restriction Requirement.
U.S. Appl. No. 11/508,662, Apr. 14, 2010, Office Action.
U.S. Appl. No. 11/508,662, Oct. 26, 2010, Office Action.
U.S. Appl. No. 11/508,715, Jan. 6, 2010, Restriction Requirement.
U.S. Appl. No. 11/508,715, Apr. 26, 2010, Office Action.
U.S. Appl. No. 11/508,715, Oct. 18, 2010, Office Action.
U.S. Appl. No. 12/365,397, Sep. 13, 2010, Restriction Requirement.
U.S. Appl. No. 12/365,397, Dec. 17, 2010, Office Action.
U.S. Appl. No. 12/365,397, Jun. 21, 2011, Notice of Allowance.
U.S. Appl. No. 12/559,377, Dec. 14, 2011, Restriction Requirement.
U.S. Appl. No. 12/559,377, Feb. 27, 2012, Office Action.
U.S. Appl. No. 12/559,377, Aug. 3, 2012, Office Action.

(56) References Cited

OTHER PUBLICATIONS

U.S. Appl. No. 13/052,634, Feb. 8, 2013, Restriction Requirement.
U.S. Appl. No. 13/052,634, Apr. 22, 2013, Office Action.
U.S. Appl. No. 13/052,634, Nov. 8, 2013, Office Action.
U.S. Appl. No. 14/532,537, Nov. 4, 2014, Sibbitt Jr. et al.
U.S. Appl. No. 11/508,662, Mar. 24, 2014, Office Action.
U.S. Appl. No. 11/508,662, Jul. 25, 2014, Notice of Allowance.
U.S. Appl. No. 11/508,715, Mar. 27, 2014, Office Action.
U.S. Appl. No. 11/508,715, Aug. 15, 2014, Office Action.
U.S. Appl. No. 12/559,377, Jul. 30, 2014, Notice of Allowance.
U.S. Appl. No. 13/052,634, Dec. 24, 2014, Office Action.

* cited by examiner

TISSUE EVERSION APPARATUS AND TISSUE CLOSURE DEVICE AND METHODS FOR USE THEREOF

BACKGROUND

1. The Field of the Disclosure

The present disclosure generally relates to tissue closure apparatuses and methods.

2. The Relevant Technology

During intravascular and other related medical procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance.

After the procedure is completed and the catheter is removed from the patient, however, the access hole must be closed to prevent hemorrhage. This is typically achieved by applying pressure over the blood vessel manually and then by applying a pressure bandage or a compressive weight. With conventional methods, the risk of post-puncture hemorrhage is high, which can cause considerable complications. The risk of complications is exacerbated by the concomitant use of anticoagulant medications such as heparin or warfarin and by anti-platelet drugs, which are commonly used following a procedure in order to prevent clot formation and thrombus and/or to treat vascular disease.

It is generally recognized that many currently employed vascular sealing methods and devices and other tissue closure methods and devices incompletely seal holes or wounds in vascular or other tissue. Achieving complete wound closure is particularly important in sealing arterial punctures, which are relatively high pressure systems. For example, under normal blood pressure, the arterial system has a pressure of about 120/80 mmHg or more. Failure to completely close arterial holes can result in hematoma, exsanguination, and in extreme cases, may result in catastrophic consequences, such as limb amputation and death. Moreover, many currently employed vascular devices employ methods and materials that remain on the intravascular endothelial surface or otherwise in the sealed vessel. Materials that remain intravascularly can be a nidus for thrombus or intravascular mural hyperplasia with later spontaneous and catastrophic closure of the vessel.

BRIEF SUMMARY

The present disclosure provides methods and apparatuses that are suitable for closure of vascular punctures or other openings in bodily tissues. The devices and methods described herein are configured for everting a portion of tissue around a puncture site for wound closure on the external surface of the wound. For example, the tissue eversion apparatus may be configured for drawing up a portion of a vessel surrounding a venous or arterial puncture and orienting the inner surface of the vessel at least partially outward so that a closure element may be placed around the everted region on the exterior surface of the vessel. Such a wound closure procedure allows wound healing with little endothelial disruption thereby reducing the chances of intravascular thrombosis or embolism or intimal hyperplasia. In some embodiments, the devices are bioabsorbable.

In one embodiment, a tissue eversion apparatus for everting tissue surrounding a tissue puncture site is disclosed. The tissue eversion apparatus includes an elongate member having a proximal end, a distal end, and an exterior surface. The tissue eversion apparatus further includes a tissue engaging portion disposed on the exterior surface of the elongate member at or near the distal end. The tissue engaging portion is configured to locate and engage a portion or portions of the tissue surrounding the puncture site as the apparatus is withdrawn relative to the puncture.

The tissue engaging portion may include an adhesive portion configured to releasably bond to an edge portion around the tissue puncture to be closed, at least two tissue engaging prongs that extend radially outward in a proximal direction and that are disposed on the exterior surface of the elongate member at or near the distal end, or a combination thereof.

In another embodiment, a system for closing a tissue puncture is described. The system includes a tissue eversion apparatus configured to form an everted tissue region, the tissue eversion apparatus including: an elongate member configured to be positioned in the tissue puncture, the elongate member having a proximal end, a distal end, and an exterior surface, and a tissue engaging portion disposed on the exterior surface of the elongate member at or near the distal end that is configured to locate and engage a portion or portions of the tissue surrounding the puncture site as the apparatus is withdrawn relative to the puncture. The system further includes a closure element configured for capturing at least a portion of the tissue everted by the tissue eversion apparatus so as to close the tissue puncture.

The closure element may include an annular or semi-annular clip configured to be closed around the everted tissue region so as to close the tissue puncture, a generally annular-shaped body disposed about a central axis, the body having an aperture extending therethrough, the body being movable between a first open position configured to receive a portion of the everted tissue in the aperture and a second closed position configured to close around the everted tissue disposed in the aperture so as to close the tissue puncture, and the like.

In yet another embodiment, a method of closing a puncture in a body tissue is described. The method includes (1) positioning a tissue eversion apparatus in the puncture, the tissue eversion apparatus being configured to form an everted tissue region around the puncture. The method further includes (2) withdrawing the tissue eversion apparatus proximally from the opening such that the tissue engaging prongs pierce the tissue and draw the tissue up to form an everted tissue region around the opening in the body tissue, (3) positioning a closure element around at least a portion of the everted tissue region so as to close the opening, and (4) releasing the everted tissue from the tissue engaging prongs.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Introduction

The present disclosure provides methods and apparatuses that are suitable for closure of vascular punctures or other openings in bodily tissues. The devices and methods described herein are configured for everting a portion of tissue around a puncture site for wound closure on the external surface of the wound. For example, the tissue eversion apparatus may be configured for drawing up (i.e., everting) a portion of a vessel surrounding a venous or arterial puncture and orienting the inner surface of the vessel at least partially outward so that a closure element may be placed around the inverted region on the exterior surface of the vessel.

As used herein, in the specification and appended claims, directional terms, such as "top," "bottom," "up," "down," "upper," "lower," "proximal," "distal," and the like are used solely to indicate relative directions in viewing the drawings and are not intended to limit the scope of the claims in any way.

II. Tissue Eversion and Closure Apparatuses

The present disclosure describes tissue eversion apparatuses and methods that can be used to evert a region of tissue around an opening in a body wall, such as a blood vessel. The present disclosure also describes tissue closure systems that include a tissue eversion apparatus and a closure element and a delivery system for delivering a closure element to the everted tissue region. Typically, with the tissue around the opening in an everted state, a closure element can be applied to the everted tissue region so as to close the opening. The apparatuses and methods described herein are configured for wound closure on the external surface of the wound, which allows wound healing with little endothelial disruption thereby reducing the chances of intravascular thrombosis or embolism or intimal hyperplasia. In some embodiments, the devices are bioabsorbable.

Generally, the apparatuses and methods described herein can be used with any type of body tissue that has sufficient strength to be everted by a tissue eversion apparatus and subsequently held together by a tissue closure element described hereinafter. By way of example only, embodiments of the present invention can be used to close openings in tissues that have a wall or membrane function, e.g., pulmonary, intestinal, vascular, urethral, gastric, renal or other wall structures, or in membranes, e.g., amniotic or pericardial membranes. Openings in other types of tissues can also be closed using embodiments of the present invention. Although many types of body tissue can be closed by the methods and apparatuses disclosed herein, the description included herein refers to "vessels" for convenience.

Figure 1A:
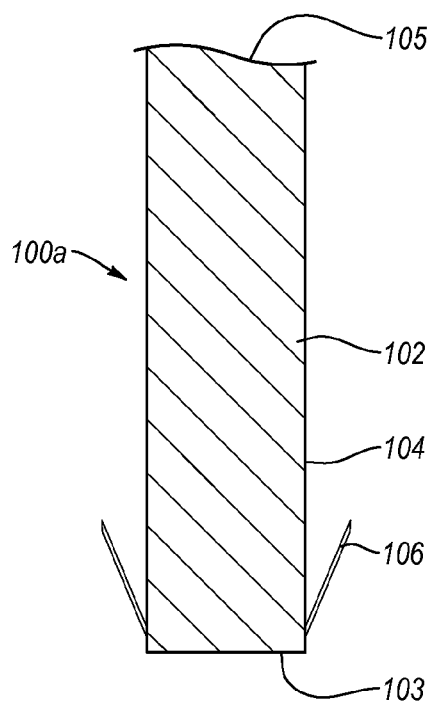
FIG. 1A illustrates a cut-away view of a first embodiment of a tissue eversion apparatus, according to one embodiment of the disclosure.

Referring now to the Figures, FIG. 1A illustrates a tissue eversion apparatus 100a according to one embodiment of the disclosure. The tissue eversion apparatus 100a includes an elongate member 102 having a proximal end 105, a distal end 103, and an exterior surface 104. The tissue eversion 100a further includes a tissue engaging portion disposed on the exterior surface 104 of the elongate member 102 at or near the distal end 103. In the case of tissue eversion apparatus 100a, the tissue engaging portion includes at least two tissue engaging prongs 106 that extend radially outward in a proximal direction. The tissue engaging prongs 106 that are positioned and configured on the exterior surface 104 of the elongate member 102 at or near the distal end 103 such that they can locate and engage a portion or portions of the tissue surrounding the puncture site as the apparatus is withdrawn relative to the puncture.

In some embodiments, the tissue engaging prongs 106 may include a hinged region (not shown), such as a flattened region or a relieved region to, for example, facilitate proximal folding of the tissue engaging prongs during storage and/or during insertion of the apparatus 100a into a puncture and distal folding of the tissue engaging prongs 106 to facilitate tissue release after a closure element has been applied to the everted tissue region. In one embodiment, the tissue engaging prongs 106 include sharpened ends such that they can pierce at least part way through the tissue to be everted.

In one embodiment, the tissue engaging prongs 106 can be fabricated from a biocompatible material. Suitable examples of biocompatible materials include, but are not limited to stainless steel (e.g., 304V and 316L stainless steels), titanium, nickel titanium alloys (e.g., binary Ni—Ti), or polymeric materials such as polyethylene terephthalate (PET), polyethylene (PE), high-density polyethylene (HDPE), polypropylene (PP), polyetheretherketone (PEEK), and the like. In some embodiments, the tissue engaging prongs 106 can be fabricated from a metal material such as stainless steel, titanium, nickel titanium alloys, or the like and coated with a polymeric material such as polytetrafluoroethylene (PTFE) to improve biocompatibility and reduce friction between the tissue engaging prongs 106 and a patient's tissue as the prongs 106 engage and disengage with the tissue. In some embodiments, the tissue engaging prongs can be formed from a shape-memory material such as a Ni—Ti to facilitate tissue engagement and tissue release. In addition, the use of shape memory materials may be advantageous in cases where the tissue eversion apparatus is to be used more than once.

In one embodiment, the tissue engaging prongs 106 can be fabricated from a wire material, such as a round drawn wire, a drawn wire having a flattened profile, or a ground wire. Alternatively, in some embodiments, the tissue engaging prongs 106 can be fabricated from tubular material similar to materials that are used to fabricate hypodermic needles. In one embodiment, the tissue engaging prongs 106 can have a cross-sectional dimension of about 0.02 mm to about 0.5 mm, about 0.05 mm to about 0.4 mm, about 0.075 mm to about 0.3 mm, about 0.1 mm to about 0.2 mm, or any dimension therebetween. It is noted, however, that the choice of the cross-sectional dimension will be dictated to a certain extent by the mechanical properties of the material used to fabricate the tissue engaging prongs 106 and the intended application of the tissue eversion apparatus 100a.

As will be described in greater detail below in reference to methods of closing a tissue opening, when the tissue engaging prongs 106 engage with the tissue surrounding the tissue opening, the tissue eversion apparatus 100a can be retracted proximally from the wound to pull up (i.e., evert) a portion of tissue surrounding the opening. When the tissue is in an everted state, a closure element, such as a staple or an annular or semi-annular ring, can be applied to the everted tissue region to seal the opening.

In one embodiment, the tissue engaging prongs 106 have a length sufficient to pierce at least part way through the tissue to be everted. One example of a body wall structure is the femoral artery, which is a common access point for a variety of transluminal procedures. The femoral artery has a wall thickness of about 1 mm to about 1.5 mm. In one embodiment, the tissue engaging prongs 106 have a length of at least about 0.25 mm, 0.5 mm, 0.75 mm, 1 mm, 1.25 mm, 1.5 mm, 2 mm, 2.5 mm, or any length therebetween. In another embodiment, the tissue engaging prongs 106 have a length in a range of about 0.25 mm to about 2.5 mm, about 0.5 mm to about 2 mm, about 0.75 mm to about 1.5 mm, or about 1 mm to about 1.5 mm.

Figure 1B:
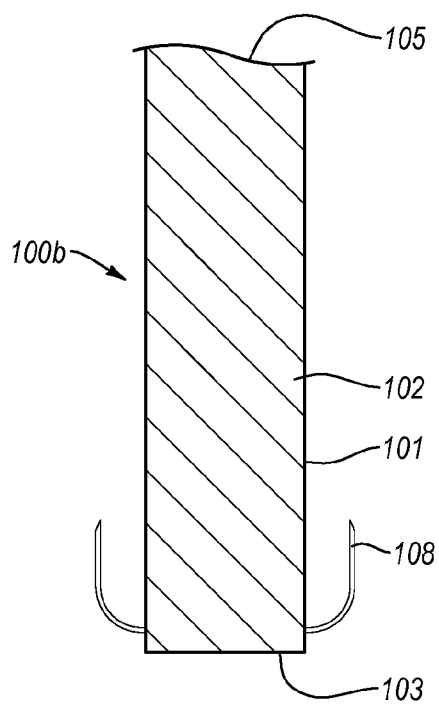
FIG. 1B illustrates a cut-away view of a second embodiment of a tissue eversion apparatus, according to one embodiment of the disclosure.

Referring now to FIG. 1B, an alternative embodiment of a tissue eversion apparatus 100b is illustrated. The tissue eversion apparatus 100b includes an elongate member 102 having a proximal end 105, a distal end 103, and an exterior surface 101. The tissue eversion apparatus 100b further includes at least two curved tissue engaging prongs 108 disposed on the exterior surface 104 of the elongate member 102 at or near the distal end 103. The tissue engaging prongs 108 curve outward and proximally from the distal end 103 of the elongate member 102. As such, the tissue engaging prongs 108 can locate and engage a portion or portions of the tissue surrounding the puncture site as the apparatus is withdrawn relative to the puncture. In some embodiments, the tissue engaging prongs 108 may include a hinged region (not shown), such as a flattened region or a relieved region to, for example, facilitate proximal and distal folding of the tissue engaging prongs 106.

Figure 1C:
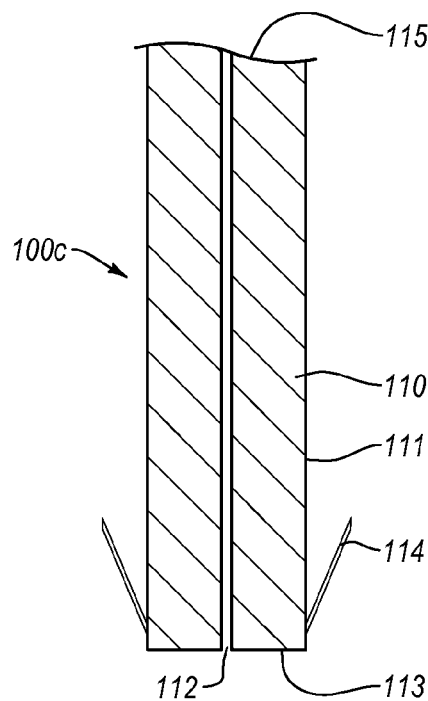
FIG. 1C illustrates a cut-away view of a third embodiment of a tissue eversion apparatus, according to one embodiment of the disclosure.

Referring now to FIG. 1C, yet another embodiment of a tissue eversion apparatus 100c is illustrated. The tissue eversion apparatus 100c includes an elongate member 110 having a proximal end 115, a distal end 113, an exterior surface 111, and at least two tissue engaging prongs 114 disposed on the exterior surface 111 of the elongate member 110 at or near the distal end 113.

The tissue eversion apparatus 100c depicted in FIG. 1C further includes an interior lumen 112. Interior lumen 112 can, for example serve as a guide wire passageway for positioning the tissue eversion apparatus 100c in a vessel, a bleed back lumen for monitoring the positioning of the tissue eversion apparatus 100c in a blood vessel, or both. While only the tissue eversion apparatus 100c depicted in FIG. 1C includes an interior lumen 112, any of the tissue eversion apparatuses or tissue closure systems described in the present disclosure can include a similar interior lumen.

Figure 1D:
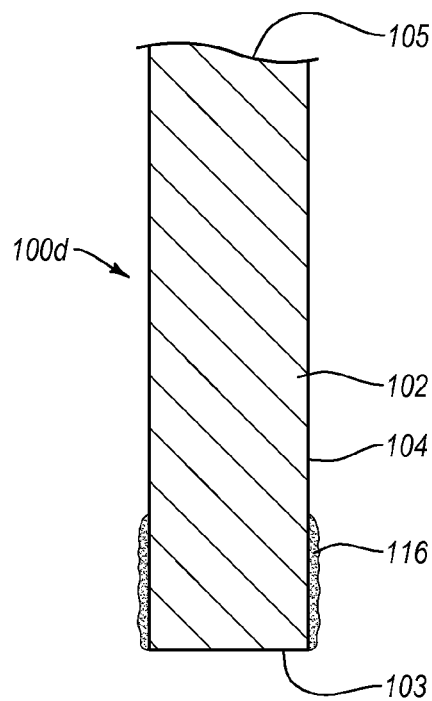
FIG. 1D illustrates a cut-away view of a fourth embodiment of a tissue eversion apparatus, according to one embodiment of the disclosure.

Referring now to FIG. 1D, yet another alternative embodiment of a tissue eversion apparatus 100d is illustrated. The tissue eversion apparatus 100a includes an elongate member 102 having a proximal end 105, a distal end 103, and an exterior surface 101. The tissue eversion apparatus 100d further includes a tissue engaging portion disposed on the exterior surface 104 of the elongate member 102 at or near the distal end 103. In the case of tissue eversion apparatus 100d, the tissue engaging portion includes an adhesive portion 116 configured to releasably bond to an edge portion around the tissue puncture to be closed. While the adhesive portion 116 can be used alone to evert the tissue around an opening, the adhesive portion 116 can be used in concert with tissue eversion prongs (e.g., prongs 106) in some embodiments to assist with everting the tissue and to assist with sealing the opening.

In one embodiment, the adhesive portion 116 may include a methacrylate glue or a similar that can form an adhesive bond with tissue surrounding an opening when the adhesive portion 116 contacts the tissue. In one embodiment, the adhesive portion 116 may include a bioadhesive derived from a marine organism or a microorganism that can form an adhesive bond with tissue surrounding an opening when the bioadhesive contacts the tissue. For example, many marine organisms produce protein-based glues and slimes that are currently being examined for use as temporary and permanent adhesives for medical applications.

Figure 2A:
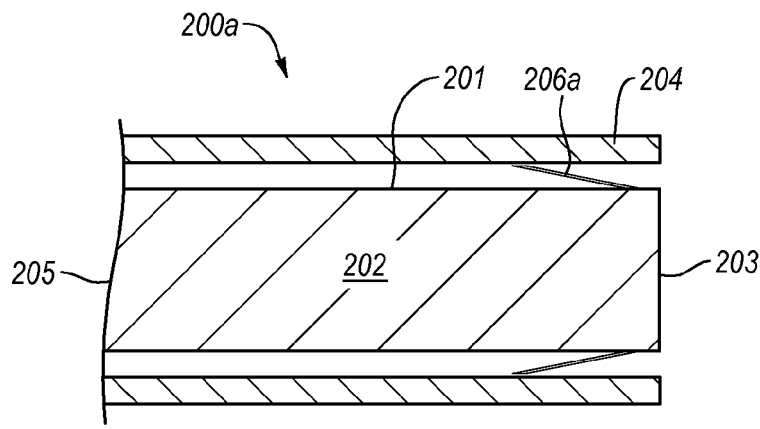
FIG. 2A illustrates an embodiment of a delivery configuration of a tissue eversion apparatus that includes an outer sheath, according to one embodiment of the disclosure.
Figure 2B:
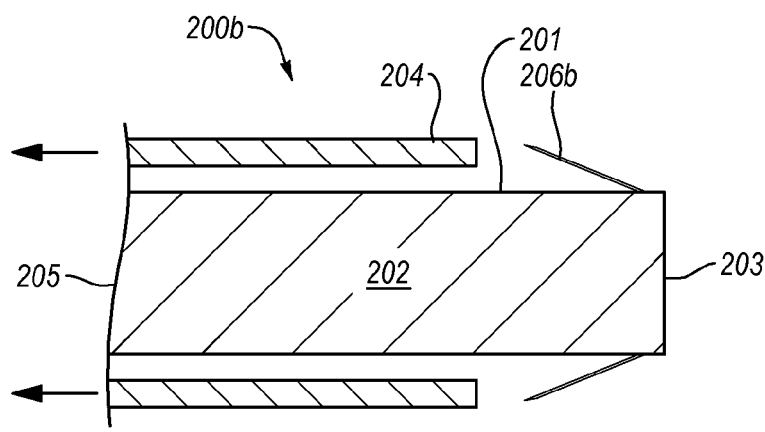
FIG. 2B illustrates the tissue eversion apparatus of FIG. 2A in a tissue engaging configuration, according to one embodiment of the disclosure.
Figure 2C:
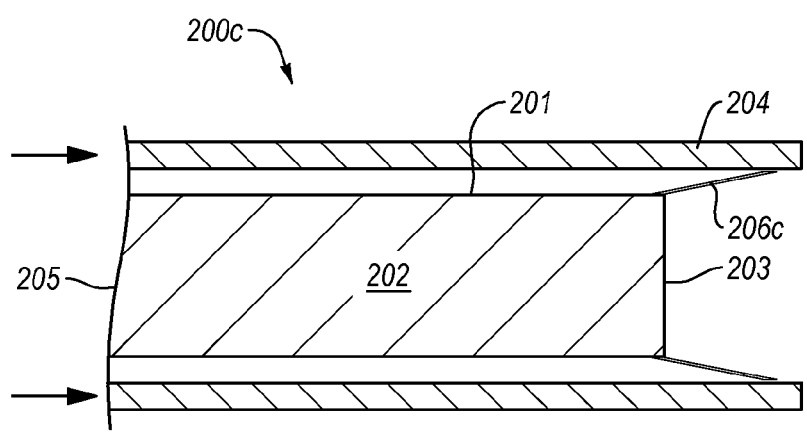
FIG. 2C illustrates the tissue eversion apparatus of FIG. 2A in a tissue releasing configuration, according to one embodiment of the disclosure.

Referring now to FIGS. 2A-2C, an embodiment of a tissue eversion apparatus that includes an outer sheath is illustrated. FIG. 2A illustrates the tissue eversion apparatus 200a in a delivery configuration, according to one embodiment of the disclosure. The tissue eversion apparatus 200a includes an elongate member 202 having a proximal end 205, a distal end 203, and an exterior surface 201. The elongate member 202 includes at least two tissue engaging prongs 206a disposed at or near the distal end of the elongate member 202.

In the delivery configuration illustrated in FIG. 2A, the outer sheath 204 is disposed substantially over the elongate member 202 and the at least two tissue engaging prongs 206a are compressed at least partially toward the outer surface 201 of the elongate member 202. Having the tissue eversion apparatus 200a in the delivery configuration allows the tissue eversion apparatus 200a to be safely inserted into the tissue and withdrawn from the tissue without the tissue eversion prongs 206a inadvertently engaging with the incorrect tissues around the puncture site (such as in the tissue tract around the puncture site or inside the vessel) and/or at the wrong time.

Referring now to FIG. 2B, the tissue eversion apparatus 200b is shown with the tissue engagement prongs 206b in a tissue engagement configuration. In the view shown in FIG. 2B, the outer sheath 204 is retracted proximally exposing tissue engagement prongs 206b, which allows the tissue engagement prongs 206b to splay outward away the exterior surface of the elongate member 202. As will be discussed in greater detail below in reference to methods for closing a tissue puncture, in the tissue engagement configuration, the tissue engagement prongs 206b are able to pierce at least part way through the tissue surrounding the tissue puncture when the tissue eversion apparatus 200b is withdrawn proximally from the tissue puncture. As such, the tissue engagement prongs 206b can engage with tissue around a puncture site to evert the tissue.

Referring now to FIG. 2C, the tissue eversion apparatus 200c is shown with the tissue engaging prongs 206c in a tissue releasing configuration. In the view shown in FIG. 2C, the tissue engaging prongs 206c in the tissue releasing configuration are shown extending distally beyond the distal end 203 of the elongate member 202 and the outer sheath 204 is pushed back down distally so that it also extends beyond the distal end 203 of the elongate member 202 and covers the distally directed tissue engaging prongs 206c.

As will be discussed in greater detail below in reference to methods for closing a tissue puncture, the pierced and everted tissue will slide off of the tissue engagement prongs 206c in the tissue releasing configuration as the tissue eversion apparatus 200b is withdrawn proximally from the tissue puncture. As will also be discussed in greater detail below in reference to methods for closing a tissue puncture, the tissue engagement prongs 206b can be transitioned from the tissue engagement configuration shown in FIG. 2B to the tissue releasing configuration shown in FIG. 2C at 206c by retracting the elongate member 202b from the tissue puncture far enough that the resistance from the tissue folds the tissue engagement prongs distally, as illustrated at 206c. Alternatively or in addition, the tissue engagement prongs can be folded distally from the configuration shown at 206b to 206c by pushing the outer sheath distally over the elongate member 202c, as shown in differences between FIGS. 2B and 2C.

Figure 3:
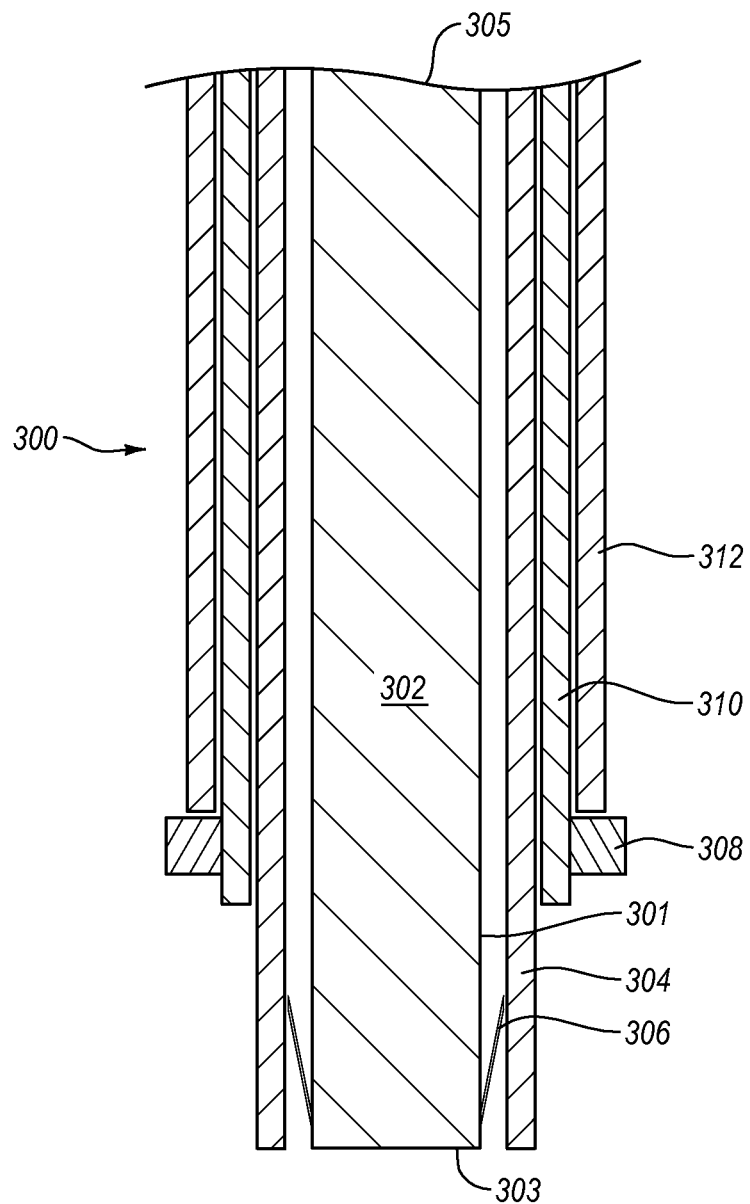
FIG. 3 illustrates an embodiment of a closure system for closing a tissue puncture, according to one embodiment of the disclosure.

Referring now to FIG. 3, an embodiment of a closure system 300 according to one embodiment of the present disclosure for closing a tissue puncture is illustrated. The closure system 300 illustrated in FIG. 3 includes a tissue eversion apparatus and a set of nested structures adapted for delivering a closure element to the tissue everted by the tissue eversion apparatus.

The closure system 300 includes an elongate member 302 having a proximal end 305, a distal end 303, an exterior surface 301, and at least two tissue engaging prongs 306 disposed on the exterior surface of the elongate member 302. The closure system 300 further includes an outer sheath 304 that, as discussed in detail with respect to FIGS. 2A-2C, is configured to transition the tissue engagement prongs 306 from a delivery configuration, to a tissue engagement configuration, and to the tissue releasing configuration. Disposed around the outer sheath 304, is a tubular member 310 that is configured to carry a closure element, shown schematically at 308. Pusher member 312 is configured to deliver the closure element 308 from the tubular member 310 to the region of tissue everted by the elongate member 302 and the at least two tissue engaging prongs 306.

In one embodiment, the elongate member 302 and the tissue engagement prongs 306 are configured to position at least a portion of the everted tissue region within the closure element 308. That is, the elongate member 302 and the tissue engagement prongs 306 are configured to draw up a portion of everted tissue and position it within the body of a closure element 308 such that the closure element 308 can be closed around the everted tissue to close the puncture.

In one embodiment, the closure element 308 may include an annular or semi-annular clip configured to be closed around the everted tissue region so as to close the tissue puncture. For example, the closure element can be a staple or staple-like element that is configured to be clamped around the everted tissue region to close the tissue puncture.

In another embodiment, the closure element 308 may include a generally annular-shaped body disposed about a central axis, such as a crown-shaped structure that is configured to fit over the everted tissue region and close the tissue puncture. The body of the closure element 308 may include an aperture extending through the body such that the elongate member 302 and the tissue engaging prongs 306 can pass a portion of the everted tissue region through the aperture. In one embodiment, the body of the annular-shaped closure element 308 is movable between a first open position configured to receive a portion of the everted tissue in the aperture and a second closed position configured to close around the everted tissue disposed in the aperture so as to close the tissue puncture.

Additional examples of closure elements that can be used to close a tissue puncture include, but are not limited to, suture loops, sutures, cincture elements, rubber band elements, and the like. For example, the everted tissue region can be drawn up into a suture loop such that the suture loop can then be closed around the everted tissue region to close the opening. Likewise, the everted tissue region can be drawn up into an open rubber band element that can then be released so it can close around the everted tissue region and seal the opening.

In one embodiment, the closure element 308 can be fabricated from a biocompatible material. Suitable examples of biocompatible materials include, but are not limited to stainless steel (e.g., 304V and 316L stainless steels), titanium, and nickel titanium alloys (e.g., binary Ni—Ti). In addition, the closure element 308 can be fabricated from a bioabsorbable material. Examples of such materials include polyglycolic acid (PGA) and it co-polymers poly(lactic-co-glycolic acid, poly(glycolide-co-caprolactone), poly(glycolide-co-trimethylene carbonate), Mg alloys, and the like. Other materials are also possible. By being fabricated from a bioabsorbable material, the closure element 308 may dissolve and become absorbed into the body after the opening in the tissue has been closed. Because the closure element 308 may be absorbed into the body, a surgeon in future procedures will not be prevented from reaccessing a similar area of the tissue as is the case with many conventional clips.

In one embodiment, the closure element 308 may include protrusions or tines that help the closure element 308 to grip the tissue and seal the tissue puncture. For example, in the case of the annular body described above, the annular body may include a plurality of tissue engaging protrusions or tines that extend from an outer region of the annular body into the aperture and generally towards a central axis of the annular body. The tissue engaging protrusions or tines can include essentially any structure that is designed to engage the tissue once the tissue has been positioned within aperture. This can include structures designed to puncture or otherwise penetrate the tissue or to structures designed to press against the tissue without penetration therein.

In one embodiment, the tissue engaging protrusions or tines have a length sufficient to pierce at least part way through the everted tissue. One example of a body wall structure that may be punctured and subsequently everted and sealed using the apparatuses and methods described herein is the femoral artery, which is a common access point for a variety of transluminal procedures. The femoral artery has a wall thickness of about 1 mm to about 1.5 mm. In one embodiment, the tissue engaging protrusions or tines that project into the annular body of the closure element have a length of at least about 0.25 mm, 0.5 mm, 0.75 mm, 1 mm, 1.25 mm, 1.5 mm, 2 mm, 2.5 mm, or any length therebetween. In another embodiment, the tissue engaging protrusions or tines have a length in a range of about 0.25 mm to about 2.5 mm, about 0.5 mm to about 2 mm, about 0.75 mm to about 1.5 mm, or about 1 mm to about 1.5 mm. Other types of tissue engaging protrusions or tines may also be used.

III. Methods for Closing a Tissue Puncture

Figure 4A:
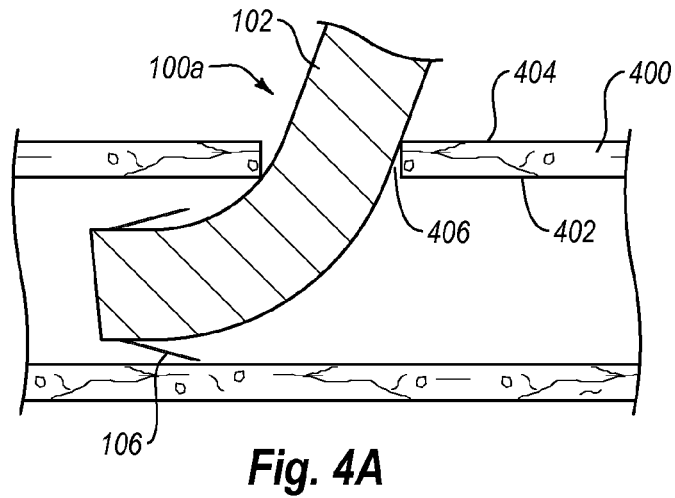
FIGS. 4A-4C illustrate a method of closing an opening in a tissue wall using the tissue eversion apparatus of FIG. 1B and a tissue closure element.
Figure 4B:
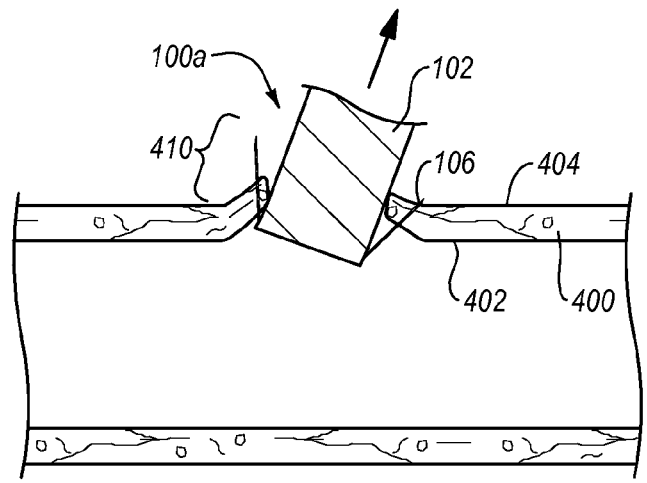
Figure 4C:
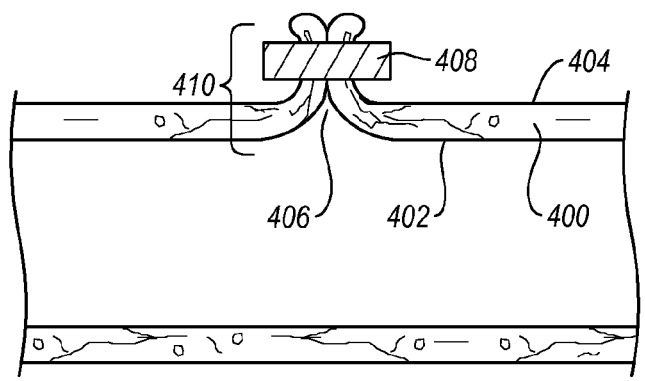

Turning to FIGS. 4A-4C, a method of sealing and/or closing a puncture in a tissue, such as puncture 406 in blood vessel 400, using the tissue eversion apparatus 100a of FIG. 1A will now be discussed. Applicant notes that all of the disclosed methods herein are exemplary only and that other methods of sealing and/or closing a tissue puncture using tissue eversion apparatus 100a can also be performed.

Initially, the tissue eversion apparatus 100a is inserted into the body so that the distal end 103 is disposed in the vessel 400, as shown in FIG. 4A. In one embodiment, a guide wire (not shown) can be used to aid in positioning the tissue eversion apparatus 100 inside the vessel 400. A bleed back lumen or other indicating method or apparatus known in the art can also be used to indicate when the tissue eversion apparatus 100a is in position.

As shown in FIG. 4B, once the tissue eversion apparatus 100a is in position in the vessel, the tissue eversion apparatus can be retracted proximally from the vessel 400. When the tissue eversion apparatus 100a is retracted proximally, the tissue engagement prongs disposed on the outer surface of the elongate member 102 pierce at least part way through the inner wall 402 of the vessel 400 toward the outer wall 404 and begin to form an everted tissue region 410.

As the tissue eversion apparatus 100a is further retracted, a closure element 408 can be applied to the everted tissue region 410. As shown in FIG. 4C, the closure element 408 is applied to the exterior surface 404 of the vessel 400 and the complementary halves of the inner surface 402 are joined together across the puncture 406. The closure element 408 can be applied to the everted tissue region 410 by a second device, such as a surgical stapling device or a suturing device, or the closure element applier can be integral to the tissue eversion apparatus 100a.

Sealing the puncture 406 on the external surface of the wound allows wound healing with little endothelial disruption thereby reducing the chances of intravascular thrombosis or embolism or intimal hyperplasia. In addition, if the closure element 408 is bioabsorbable, sealing on the exterior surface of the wound allows the closure element to bioabsorb without danger of the closure element disintegrating and casting off emboli into the circulatory system.

Turning to FIGS. 5A-5G, a method of sealing and/or closing a tissue puncture using the closure system 300 of FIG. 3 is illustrated. Applicant notes that all of the disclosed methods herein are exemplary only and that other methods of sealing and/or closing a tissue puncture using the tissue closure system 300 can also be performed.

Figure 5A:
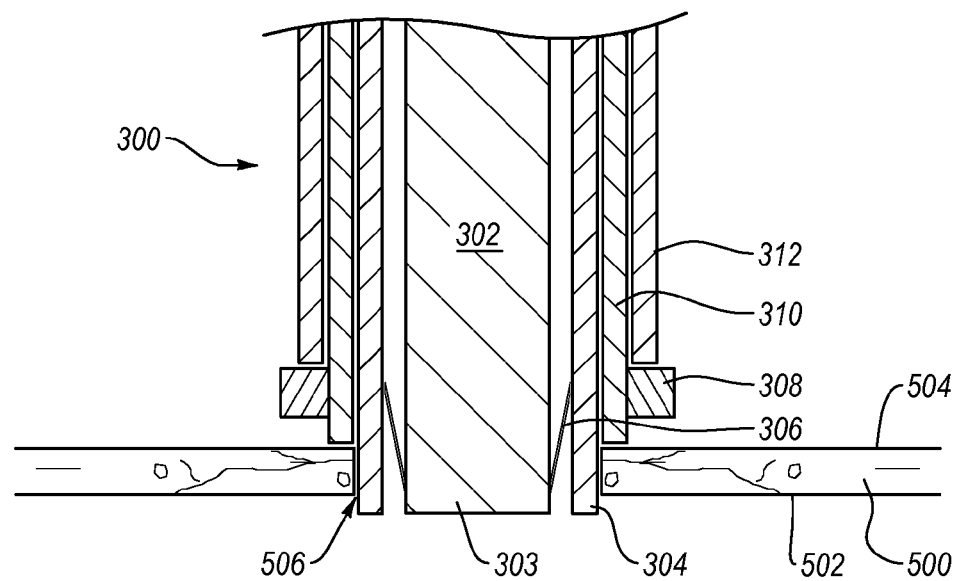
FIGS. 5A-5G illustrate a method of closing an opening in a tissue wall using the tissue closure system of FIG. 3.

As shown in FIG. 5A, tissue closure system 300 is inserted into the puncture 506 in the vessel 500 so that the distal end 303 of the elongate member 302 and the outer sheath are in the vessel 500 and the tubular member 310 abuts the outer surface 504 of vessel 500. A guide wire (not shown) can be used to aid in positioning tissue closure system 300, as is known in the art. A bleed back lumen or other indicating method or apparatus known in the art can also be used to indicate when tissue closure system 300 is in position.

Figure 5B:
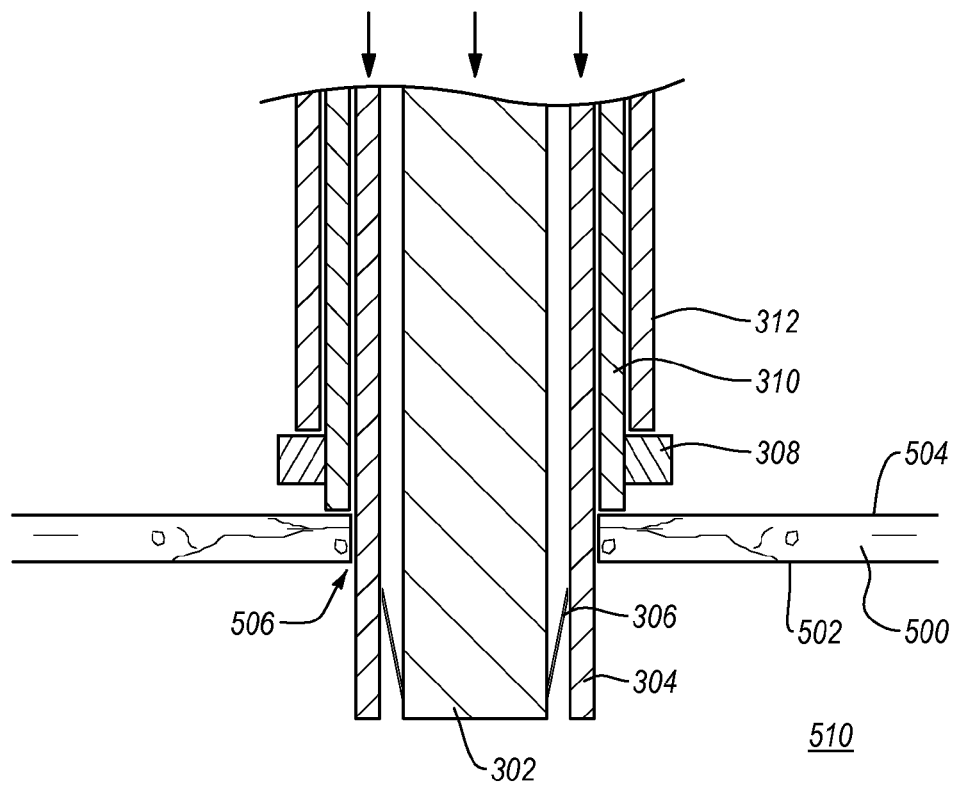

As shown in FIG. 5B, once tissue closure system 300 is in position in the puncture 506 in the vessel 500, an external force, denoted by the downward arrows, is then applied to the elongate member 302 and the outer sheath 304 by pushing distally on the elongate member 302 and the outer sheath 304 or another actuating device. The external force causes the elongate member 302 and the outer sheath 304 to extend through the puncture 506 and into vessel lumen 510 such that the tissue engaging prongs 306 are completely contained in the vessel lumen 510.

Figure 5C:
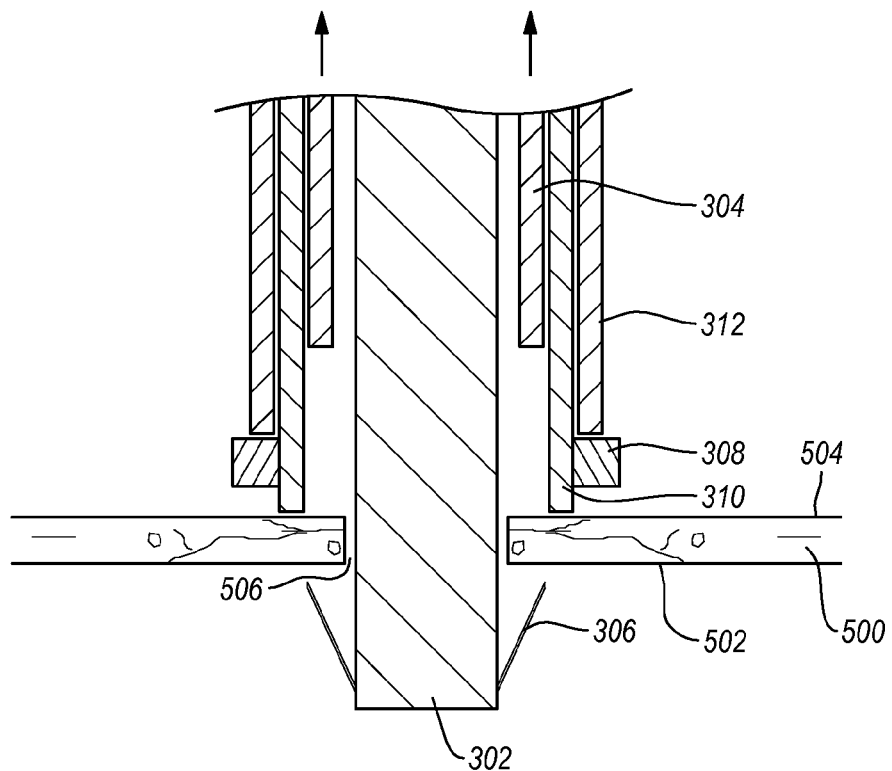

As shown in FIG. 5C, once the elongate member 302, the outer sheath 304, and the tissue engaging prongs 306 are disposed in the vessel lumen 510, the outer sheath 304 may be retracted proximally, as indicated by the upward arrow. This exposes the tissue engaging prongs 306 and allows them to expand into a state such that they can locate and engage a portion or portions of the tissue surrounding the puncture site 506 as the elongate member 302 is withdrawn relative to the puncture 506.

Figure 5D:
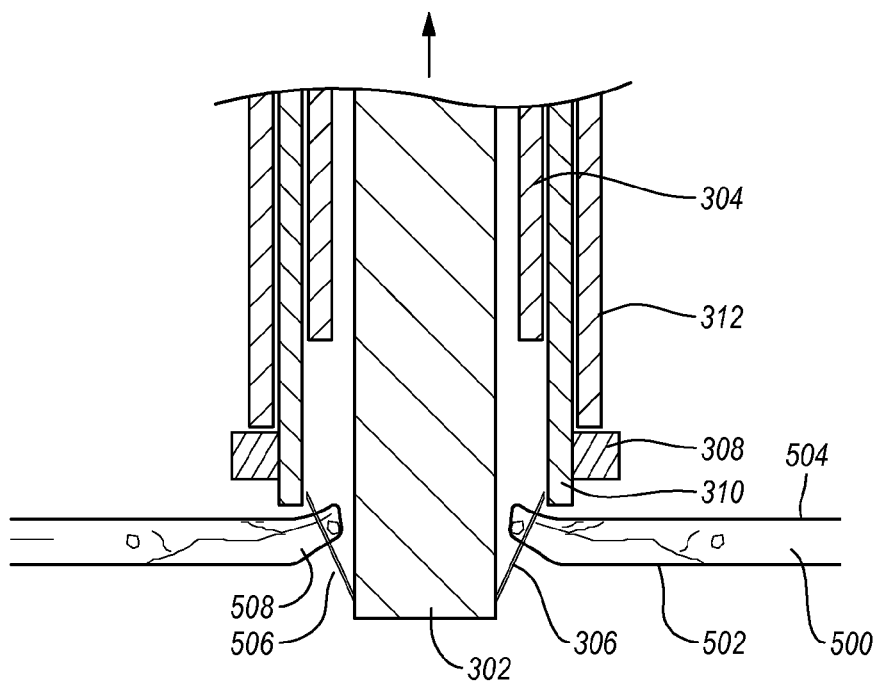
Figure 5E:
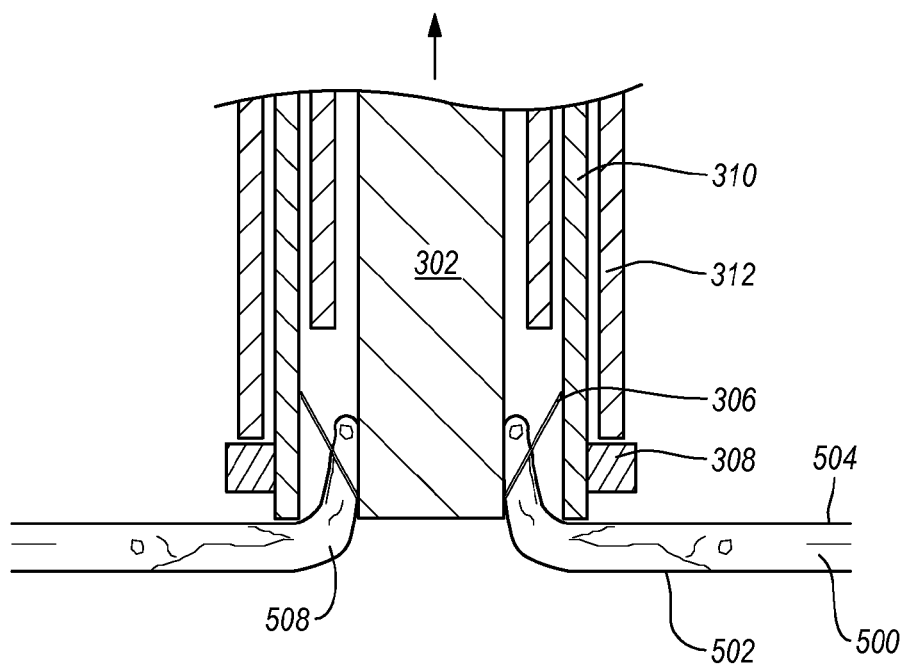

Referring now to FIG. 5D, an external proximal retracting force, denoted by the upward arrow in FIG. 5D, may then be applied to the elongate member 302. This causes the expanded tissue engaging prongs to pierce through the inner surface 502 of the vessel 500 around the opening 506 and to begin to form the everted tissue region 508. As the external retracting force is maintained on the elongate member 302, the everted tissue region 508 is drawn proximally and inward into the tubular member 310, as shown in FIG. 5E. Because the closure element 308 is disposed on the outside of the tubular member, the everted tissue region 508 is effectively drawn proximally and inward into the closure element 308 as well.

Figure 5F:
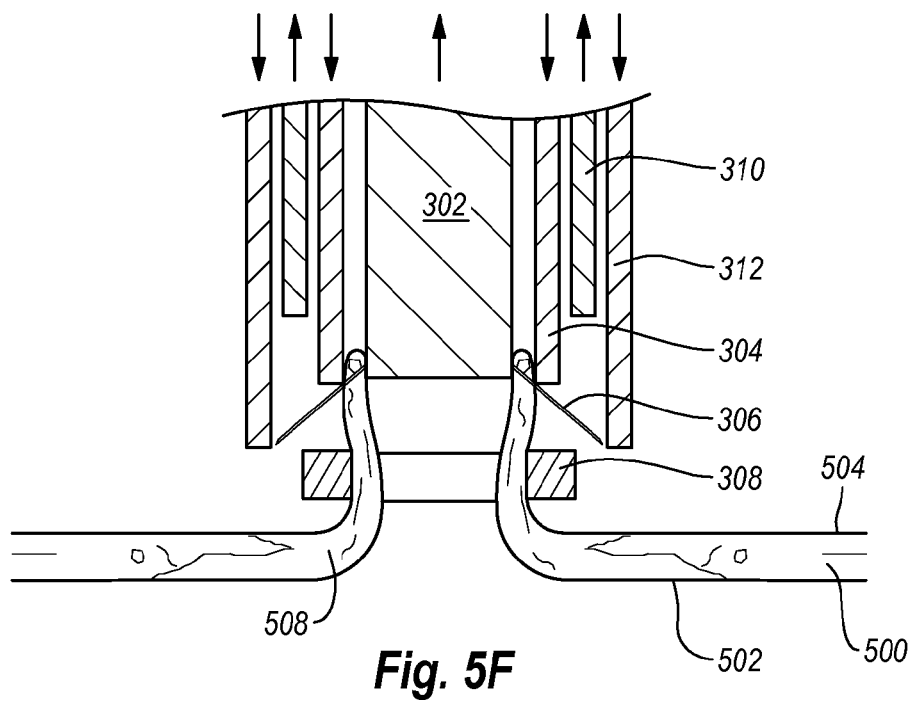
Figure 5G:
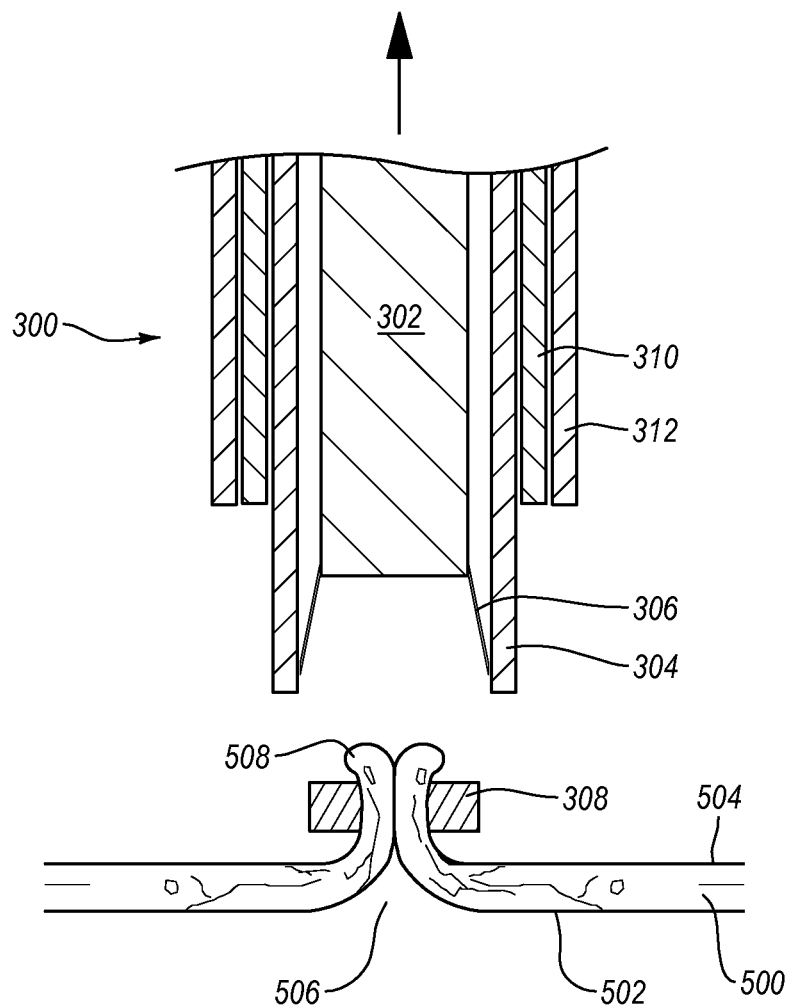

Referring now to FIG. 5F, the external proximal retracting force on the elongate member 302 is maintained. The closure element 308 is deployed from tubular member 310 onto the everted tissue region 508 by pusher member 312 pushing the closure element 308 off of the tubular member 310. The closure element 308 can then close, such as by a shape memory effect, or be closed, such as by a clip applier (not shown), around the everted tissue region 508.

Simultaneously or nearly simultaneously with the deployment of the closure element 308, the outer sheath is pushed down distally to assist in folding the tissue engagement prongs 306 distally so as to transition the tissue engagement prongs 306 to a tissue releasing configuration.

Once the tissue engagement prongs 306 have disengaged from the everted tissue region, the tissue closure system 300 can be removed from the body. As the tissue closure system 300 is removed, the closure element 308 can close or can be closed by a clipping device to seal the puncture. If the closure element 308 is made of a bioabsorbable material, the closure element 308 will dissolve and be absorbed into the body after the tissue has grown together over opening 506. This can aid the surgeon in future procedures by allowing the surgeon to reaccess a similar area of the tissue without having to remove or avoid the clip.

While a shape memory, generally annular closure element 308 is shown in FIGS. 5A-5G, this should not be taken to limit the scope of the disclosure in any way. As noted above, may types of closer elements can be adapted to seal the opening in the tissue.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method of closing a puncture in a body tissue having an inner wall and an outer wall, the method comprising:
   positioning a tissue eversion apparatus in an opening of the puncture, the tissue eversion apparatus being configured to form an everted tissue region around the puncture, the tissue eversion apparatus including:
      a solid elongate member configured to be positioned in the puncture, the elongate member having a proximal end, a distal end, a distal surface, and an exterior surface extending between the distal end and the proximal end, the distal surface abutting the exterior surface at the distal end; and
      a tissue engaging portion comprising at least two tissue engaging prongs that extend radially outwardly in a proximal direction and that are disposed on the exterior surface of the elongate member at or near the distal end and on opposite sides of the elongate member, wherein the at least two tissue engaging prongs are configured to locate and engage a portion or portions of the tissue surrounding the puncture, and on opposite lateral sides of the opening, as the apparatus is withdrawn relative to the puncture;

withdrawing a portion of the tissue eversion apparatus, which has previously passed through the opening to position the tissue eversion apparatus, proximally from the opening such that the tissue engaging prongs pierce the tissue from the inner wall towards the outer wall and draw the tissue up to form an everted tissue region around the opening in the body tissue, the tissue engaging prongs extending proximally and radially outwardly from the elongate member in a pre-deployed configuration and following engagement with the tissue and withdrawal of the elongate member proximally to form the everted tissue;

positioning a closure element around at least a portion of the everted tissue region so as to close the opening; and releasing the everted tissue region from the tissue engaging prongs.

2. The method of claim 1, wherein releasing the everted tissue region from the tissue engaging prongs comprises:
further withdrawing the tissue eversion apparatus from the opening so as to fold the tissue engaging prongs distally along the exterior surface of the elongate member.

3. The method of claim 1, wherein the closure element is disposed on the exterior surface of the elongate member and deliverable therefrom.

4. The method of claim 1, wherein the closure element is disposed on the exterior surface of a tubular member that is disposed around the elongate member.

5. The method of claim 1, wherein the tubular member is associated with a pusher member configured to push the closure element off of the tubular member and onto the everted tissue region.

6. The method of claim 1, wherein positioning a closure element around at least a portion of the everted tissue region further comprises withdrawing the tissue eversion apparatus from the puncture so as to position at least a portion of the everted tissue region within an opening in the closure element and closing the opening in the closure element so as to close the tissue puncture.

7. The method of claim 6, wherein the closure element comprises a shape memory alloy.

8. The method of claim 1, wherein the tissue eversion apparatus further comprises an outer sheath configured to be disposed over the tissue engaging portion in a first position and configured to be retracted to expose the tissue engaging portion in a second position.

9. The method of claim 1, wherein the elongate member of the tissue eversion apparatus further comprises a bleed-back lumen configured to facilitate positioning of the tissue eversion apparatus inside a blood vessel.

10. The method of claim 1, wherein positioning a closure element around at least a portion of the everted tissue region further comprises closing an annular or semi-annular ring around at least a portion of the everted tissue region.

11. A method of closing a puncture in a body tissue having an inner wall and an outer wall, the method comprising:
positioning a tissue eversion apparatus configured to form an everted tissue region around the puncture, the tissue eversion apparatus including:
a tubular member;
a solid elongate member disposed within the tubular member and being configured to be positioned in the puncture, the elongate member having a proximal end, a distal end, and an exterior surface, the exterior surface being a curved surface of the elongated member extending between the proximal end and the distal end; and at least two tissue engaging prongs extending radially outwardly in a proximal direction from the exterior surface of the elongate member at or near the distal end and with the at least two engaging prongs being opposite each other across the elongate member, in a linear fashion from a base mounted to the exterior surface to a tip of each prong, the at least two tissue engaging prongs are configured to locate and engage a portion or portions of the tissue surrounding the puncture as the apparatus is withdrawn proximally relative to the puncture;

advancing the elongate member distally through the puncture and from the tubular member from a pre-deployed configuration to a deployed configuration prior to engagement with the tissue, the tissue engaging prongs extending proximally and radially outwardly from the elongate member in both the pre-deployed configuration and the deployed configuration;

withdrawing a portion of the tissue eversion apparatus proximally from the puncture such that the tissue engaging prongs pierce the tissue from the inner wall to exit through the outer wall at portions of tissue surrounding the puncture and on opposite lateral sides of the puncture and draw the tissue up to form an everted tissue region around the puncture in the body tissue, the tissue engaging prongs extending proximally and radially outwardly from the elongate member in the pre-deployed configuration, following engagement with the tissue, and withdrawal of the elongate member proximally to form the everted tissue;

positioning a closure element around at least a portion of the everted tissue region so as to close the puncture; and releasing the everted tissue region from the tissue engaging prongs.

12. The method of claim 11, wherein releasing the everted tissue region from the tissue engaging prongs comprises further withdrawing the tissue eversion apparatus from the puncture to fold the tissue engaging prongs distally along the exterior surface of the elongate member.

13. The method of claim 11, wherein the tubular member is associated with a pusher member configured to push the closure element off of the tubular member and onto the everted tissue region.

14. The method of claim 11, wherein positioning a closure element around at least a portion of the everted tissue region further comprises withdrawing the tissue eversion apparatus from the puncture so as to position at least a portion of the everted tissue region within an opening in the closure element and closing the opening in the closure element so as to close the tissue puncture.

15. The method of claim 11, wherein the tissue eversion apparatus further comprises an outer sheath configured to be disposed over the tissue engaging portion in a first position and configured to be retracted to expose the tissue engaging portion in a second position.

16. The method of claim 11, wherein the elongate member of the tissue eversion apparatus further comprises a bleed-back lumen configured to facilitate positioning of the tissue eversion apparatus inside a blood vessel.

17. The method of claim 11, wherein positioning a closure element around at least a portion of the everted tissue region further comprises closing an annular or semi-annular ring around at least a portion of the everted tissue region.

18. A method of closing a puncture in a body tissue having an inner wall and an outer wall, the method comprising:

positioning a tissue eversion apparatus configured to form an everted tissue region around the puncture, the tissue eversion apparatus including:
- a tubular member;
- a solid elongate member disposed within the tubular member and being configured to be positioned in the puncture, the elongate member having a proximal end, a distal end, and an exterior surface extending from the proximal end to the distal end; and
- a plurality of tissue engaging prongs extending radially outwardly in a proximal direction from the exterior surface of the elongate member proximal to the distalmost end, in a linear fashion from a base mounted to the exterior surface to a tip of each prong, pairs of the plurality of the tissue engaging prongs being on opposite sides of the elongate member and opposite each other across the elongate member, the tissue engaging prongs are configured to locate and engage a portion or portions of the tissue surrounding the puncture, with pairs of the plurality of the tissue engaging prongs engaging with the portion or portions of the tissue on opposite lateral sides of the puncture, as the apparatus is withdrawn proximally relative to the puncture;

advancing the elongate member distally through the puncture and from the tubular member from a pre-deployed configuration to a deployed configuration prior to engagement with the tissue, the tissue engaging prongs extending proximally and radially outwardly from the elongate member in both the pre-deployed configuration and the deployed configuration, the radial extension of the tissue engaging prongs being greater in the deployed than the pre-deployed configuration;

withdrawing a portion of the tissue eversion apparatus proximally from the puncture such that the tissue engaging prongs pierce from the inner wall to exit through the outer wall the tissue and draw the tissue up to form an everted tissue region around the puncture in the body tissue, the tissue engaging prongs extending proximally and radially outwardly from the elongate member in the pre-deployed configuration, following engagement with the tissue, and withdrawal of the elongate member proximally to form the everted tissue;

positioning a closure element around at least a portion of the everted tissue region so as to close the puncture; and releasing the everted tissue region from the tissue engaging prongs by advancing the tubular member relative to the elongate member in a distal direction so as to move the tissue engaging prongs by pivoting the tissue engaging prongs about the base from the deployed configuration, in which the tissue engaging prongs extend in a proximal direction, to a release configuration, in which the tissue engaging prongs extend in a distal direction, and then withdrawing the tissue eversion apparatus from the puncture.

19. The method of claim 18, wherein releasing the everted tissue region from the tissue engaging prongs comprises folding the tissue engaging prongs distally along the exterior surface of the elongate member.

20. The method of claim 19, wherein positioning a closure element around at least a portion of the everted tissue region further comprises withdrawing the tissue eversion apparatus from the puncture so as to position at least a portion of the everted tissue region within an opening in the closure element and closing the opening in the closure element so as to close the tissue puncture.

21. The method of claim 20, wherein the tissue eversion apparatus further comprises an outer sheath configured to be disposed over the tissue engaging portion in a first position and configured to be retracted to expose the tissue engaging portion in a second position.

22. The method of claim 21, wherein the elongate member of the tissue eversion apparatus further comprises a bleedback lumen configured to facilitate positioning of the tissue eversion apparatus inside a blood vessel.

23. The method of claim 22, wherein positioning a closure element around at least a portion of the everted tissue region further comprises closing an annular or semi-annular ring around at least a portion of the everted tissue region.

* * * * *